United States Patent [19]

Maniar

[11] Patent Number: 5,886,030
[45] Date of Patent: Mar. 23, 1999

[54] USE OF VITAMIN E TOCOPHERYL DERIVATIVES IN OPHTHALMIC COMPOSITIONS

[75] Inventor: Manoj L. Maniar, San Diego, Calif.

[73] Assignee: Alcon Laboratories, Inc., Fort Worth, Tex.

[21] Appl. No.: 530,516

[22] Filed: Sep. 19, 1995

Related U.S. Application Data

[63] Continuation-in-part of Ser. No. 240,057, May 6, 1994, abandoned.

[51] Int. Cl.⁶ .................................................. A61K 31/355
[52] U.S. Cl. ............................................ 514/458; 514/912
[58] Field of Search ...................................... 514/458, 912

[56] References Cited

U.S. PATENT DOCUMENTS

| | | | |
|---|---|---|---|
| 2,680,749 | 6/1954 | Cawley et al. | 260/345.5 |
| 3,102,078 | 8/1963 | Robeson | 167/81 |
| 4,043,932 | 8/1977 | Fresenius et al. | 252/95 |
| 4,136,173 | 1/1979 | Pramoda et al. | 424/177 |
| 4,136,177 | 1/1979 | Lin et al. | 424/211 |
| 4,559,343 | 12/1985 | Han et al. | 514/264 |
| 4,861,760 | 8/1989 | Mazuel et al. | 514/54 |
| 4,911,920 | 3/1990 | Jani et al. | 424/78 |
| 4,960,799 | 10/1990 | Nagy | 514/567 |
| 5,013,751 | 5/1991 | Gerson et al. | 514/448 |
| 5,093,126 | 3/1992 | Jani et al. | 424/428 |
| 5,179,122 | 1/1993 | Greene et al. | 514/458 |
| 5,198,432 | 3/1993 | Fariss | 514/182 |
| 5,212,162 | 5/1993 | Missel et al. | 514/54 |
| 5,223,268 | 6/1993 | Stetsko et al. | 424/490 |
| 5,364,631 | 11/1994 | Janoff et al. | 424/450 |
| 5,403,841 | 4/1995 | Lang et al. | 514/226.8 |
| 5,558,876 | 9/1996 | Desai et al. | 424/427 |
| 5,559,157 | 9/1996 | Kawashima et al. | 514/777 |

FOREIGN PATENT DOCUMENTS

| | | |
|---|---|---|
| 2088927 | 8/1994 | Canada . |
| 0 380 367 A1 | 1/1990 | European Pat. Off. . |
| 0 539 215 A1 | 4/1993 | European Pat. Off. . |
| 0 578 077 A3 | 1/1994 | European Pat. Off. . |
| 61-860184127 | 8/1987 | Japan . |
| 1128921 | 5/1989 | Japan . |
| 920068343 | 3/1992 | Japan . |
| 93-37406 | 6/1993 | Japan . |
| WO 89/03689 | 5/1989 | WIPO . |
| WO 93/03720 | 3/1993 | WIPO . |
| WO 93/05794 | 4/1993 | WIPO . |
| WO 93/12761 | 7/1993 | WIPO . |
| WO 95/31217 | 11/1995 | WIPO . |
| WO 96/36316 | 11/1996 | WIPO . |

OTHER PUBLICATIONS

Carini et al., "Comparative Evaluation of the Antioxidant Activity of α–Tocopherol, α–Tocopherol Polyethylene Glycol 1000 Succinate and α–Tocopherol Succinate Isolated Hepatocytes and Liver Microsomal Suspensions," *Biochemical Pharmacology*, vol. 39 (10), pp. 1597–1601(1990).

Wu et al., "Characterization of d–Alpha Tocopheryl Polyethylene Glycol–1000 Succinate (TPGS) for Applications as an Absorption Enhancer," Eastman Technical Papers—Presented in 1994 AAPS Meeting in San Diego, CA and 1994 Pharm Tech Conference in Atlantic City, NJ.

Wu et al., "D–Alpha Tocopheryl Polyethylene Glycol 1000 Succinate (TPGS) as an Absorption Enhancer," Proc. 1st World Meeting AGPI/APV, Budapest, May 9–11, 1995.

Popovici et al., "Formulations and In Vivo Tests of Oily Indomethacin Eyedrops," *STP Pharma SCI (France)*, vol. 3(3), pp. 266–270 (1993).

Sokol, R.J. et al., "Improvement of Cyclosporin Absorption in Children after Liver Transplantation by Means of Water–soluble Vitamin E," *The Lancet*, 338, pp. 212–215 (1991).

Argao, E.A., et al., "d–α–Tocopheryl Polyethylene Glycol–1000 Succinate Enhances the Absorption of Vitamin D in Chronic Cholestatic Liver Disease of Infancy & Childhood," *Pediatric Res.*, 31(2):1, pp. 146–150 (1992).

Adams, M.W., "D–AlphaTocopheryl Polyethylene (Eastman Vitamin E TPGS) as an Emulsifier and Bio–Enhancer for Drugs and Lipophilic Compounds," *J. Congr. Int. Technol. Pharm. 6th;* 4, pp. 254–262 (1992).

Braha et al., "Ophthalmic Solution for Treatment of Sclero–keratitis and Acute Macular Oedema," WPIDS C93–117439 (1992).

Sugita et al.; "Anti–inflammatory analgesic topical preparations of indomethacin containing vitamin E or its acetate," *Chemical Abstracts*, vol. 120 (1994).

Popovici I. et al.,; "Formulation Et Essais In Vivo De Collyres Huileux D'Indometacine," STP Pharma Sci. (France), vol. 3, No. 3, pp. 266–270, (1993).

Carini et al., "Comparative Evaluation of the Antioxidant Activity of α–Tocopherol, α–Tocopherol Polyethylene Glycol 1000 Succinate and α–Tocopherol Succinate in Isolated Hepatocytes and Liver Microsomal Suspensions," *Biochemical Pharmacology*, vol. 39(10), pp. 1597–1601, (1990).

Eastman Fine Chemicals Product Brochure (1994).

"Eastman Vitamin E TPGS," Publication No. EFC–213 (1991).

*Primary Examiner*—Zohreh Fay
*Attorney, Agent, or Firm*—Patrick M. Ryan

[57] ABSTRACT

Disclosed are ophthalmic compositions containing vitamin E tocopheryl derivatives which are comfortable and non-irritating. In addition, these vitamin E tocopheryl derivatives significantly increase the aqueous solubility of certain poorly soluble ophthalmic agents.

9 Claims, No Drawings

5,886,030

USE OF VITAMIN E TOCOPHERYL DERIVATIVES IN OPHTHALMIC COMPOSITIONS

This application is a continuation-in-part application of application Ser. No. 08/240,057 filed May 6, 1994, now abandoned.

BACKGROUND OF THE INVENTION

The present invention relates generally to ophthalmic compositions. In particular, the present invention relates to the use of certain vitamin E tocopheryl derivatives to provide comfortable, non-irritating ophthalmic compositions. In addition, the present invention relates to the use of these vitamin E tocopheryl derivatives to increase the solubility of poorly soluble ophthalmic agents in aqueous compositions. For purposes of the present specification, the vitamin E tocopheryl derivatives useful in the present invention shall be referred to as "vitamin E tocopheryl derivatives" or "vitamin E derivatives" or "TPGS."

Stinging and burning sensations, as well as general discomfort, are often associated with the topical ophthalmic application of certain types of ophthalmic agents. It is believed that such ocular discomfort is due to the presence of certain functional groups in these agents. Examples of such agents which produce ocular discomfort include, but are not limited to: β-blockers such as betaxolol; prostaglandins and prostaglandin derivatives; muscarinics such as pilocarpine; α-adrenergics such as epinephrine, clonidine and apraclonidine; cholinergics such as carbachol; and non-steroidal anti-inflammatory drugs ("NSAIDs") such as diclofenac and suprofen.

There have been a number of attempts to formulate topical ophthalmic compositions to reduce the inherent discomfort associated with these ophthalmic agents. Such attempts include those described in U.S. Pat. No. 4,559,343 (Han et al.), U.S. Pat. No. 4,911,920 (Jani et al.), U.S. Pat. No. 5,093,126 (Jani et al.), and U.S. Pat. No. 5,212,162 (Missel et al.). Han et al. describe the addition of xanthine derivatives, such as caffeine, to decrease the stinging associated with topical ocular application of NSAIDs. The two Jani et al. references teach the addition of certain ion-exchange resins to compositions of β-blockers to increase comfort and to provide sustained release. Missel et al. teach combinations of gelling polysaccharides and finely-divided drug carrier substrates ("DCS") which provide comfortable and sustained release ophthalmic compositions.

In addition, U.S. Pat. No. 4,960,799 (Nagy), discloses storage stable aqueous ophthalmic compositions containing diclofenac and/or its pharmaceutically acceptable salts. The Nagy compositions include EDTA and a solubilizer such as ethoxylated castor oil.

SUMMARY OF THE INVENTION

It has now been unexpectedly discovered that the addition of certain vitamin E tocopheryl derivatives to ophthalmic compositions renders such compositions very comfortable and non-irritating. It has also been discovered that these vitamin E derivatives greatly enhance the aqueous solubility of many compounds which are only sparingly soluble in aqueous compositions.

DETAILED DESCRIPTION OF THE INVENTION

Vitamin E tocopheryl derivatives are water-soluble, biologically-active vitamin E analogues. These vitamin E derivatives have been used as alternatives to vitamin E, especially where water-solubility is desired. In addition, U.S. Pat. No. 3,102,078 describes the use of these derivatives to solubilize naturally-occurring water-insoluble vitamins, such as vitamins A, D and E. The use of these vitamin E derivatives to enhance the absorption of vitamin A and cyclosporin have also been reported. See, for example, Sokol, R. J. et al., "Improvement of Cyclosporin Absorption in Children after Liver Transplantation by Means of Water-soluble Vitamin E," *The Lancet*, 338:212–215 (1991), and Argao, E. A. et al., "d-α-Tocopheryl Polyethylene Glycol-1000 Succinate Enhances the Absorption of Vitamin D in Chronic Cholestatic Liver Disease of Infancy and Childhood," *Pediatric Res.*, 31(2) :146–150 (1992).

The vitamin E tocopheryl derivatives useful in the compositions of the present invention are highly water-soluble polyoxyalkylene glycol esters of vitamin E tocopheryl esters of a dicarboxylic acid. Representative esters of this type include the polyoxyethylene glycol esters of vitamin E tocopheryl esters of a dicarboxylic acid wherein the polyoxyethylene glycol moiety of the ester (sometimes merely referred to as the polyoxyethylene glycol moiety of the ester) has a molecular weight in the range from about 600 to about 6000, preferably in the range from about 600 to about 1500. Such esters and methods for their preparation are disclosed in U.S. Pat. No. 2,680,749 (Cawley et al.). The most preferred ester is the α-tocopheryl polyoxyethylene glycol (1000) succinate, a polyoxyethylene glycol ester of α-tocopheryl succinate wherein the polyoxyethylene glycol moiety of the molecule has an average molecular weight of about 1000.

In general, one or more vitamin E derivatives are used in the compositions of the present invention in an amount less than about 30 percent by weight (wt %). If the vitamin E derivatives are used as solubilizing agents, it is preferred to use an amount between about 0.1 and about 20 wt %, most preferably between about 0.1 and about 5 wt %. When the vitamin E derivatives are used to enhance comfort, it is preferred to use an amount between about 0.1 and about 20 wt %, most preferably between about 0.5 and about 10 wt %.

Suitable ophthalmic agents which may be included in the compositions of the present invention and administered via the method of the present invention include, but are not limited to, the racemic and enantiomeric forms and ophthalmically acceptable salts and esters of following types of compounds:

glaucoma agents, such as: β-blockers (e.g., betaxolol, timolol, and carteolol); α-agonists (e.g., apraclonidine and related 2-substituted amino imidazolines); carbonic anhydrase inhibitors; dopamine agonists and antagonists; miotic cholinergics (e.g., pilocarpine and carbachol); prostaglandins and prostaglandin derivatives; ACE inhibitors; steroids (e.g., glucocorticoids and angiostatic steroids); and calcium channel blockers;

anti-hypertensives;

non-steroidal anti-inflammatory agents, including but not limited to those classified as aryl- or heteroaryl- alkanoic acids such as diclofenac, flurbiprofen, suprofen, ketorolac, indomethacin and ketoprofen;

steroidal anti-inflammatory agents, such as fluorometholone, dexamethasone, prednisolone, tetrahydrocortisol and triamcinolone;

anti-bacterials and anti-infectives, such as aminoglycosides (e.g., tobramycin); quinolones (e.g., ciprofloxacin and ofloxacin); beta-lactams (e.g., cephalosporins such as cefamandole);

anti-fungals, such as natamycin;
anti-virals, such as acyclovir and ganciclovir;
anti-cataract agents and anti-oxidants;
anti-allergics;
anti-metabolites, such as 5-fluorouracil (5-FU) and methotrexate;
immunosuppressants, such as cyclosporin, FK-506 and leflunimide;
growth factors such as EGF, FGF, PDGF; and
prodrugs of the drug classes listed above.

Combinations of ophthalmic agents may also be used in the compositions of the present invention. Further, in formulations without ophthalmic agents, the present invention may also serve to supplement tears in the prevention or treatment of dry eye.

The compositions of the present invention may additionally include other ophthalmically acceptable components: for example, buffers (e.g., phosphate, borate and citrate), chelating agents (e.g., EDTA), preservatives, (e.g., benzalkonium chloride, Polyquad® and Dymed®) and tonicity agents (e.g., sodium chloride and mannitol). The compositions of the present invention may also include viscosity modifying agents such as: cellulosic ethers, such as, hydroxypropyl methyl cellulose (HPMC), hydroxyethyl cellulose (HEC), ethyl hydroxyethyl cellulose, hydroxypropyl cellulose, methyl cellulose, and carboxymethyl cellulose; carbomers (Carbopol ); polyvinyl alcohol; polyvinyl pyrrolidone; alginates; carrageenans; and guar, karaya, agarose, locust bean, tragacanth and xanthan gums. The concentration of such viscosity modifiers will vary between about 0.1 to about 5 wt %, but such formulations will generally have a viscosity between about 10 and about 1000 centipoise.

The ophthalmic compositions containing TPGS may additionally contain polymers which will undergo sol-to-gel transition upon exposure to physical or chemical stimuli, such as changes in pH, ion concentration, and/or temperature.

The ophthalmic agents contained in the compositions of the present invention may optionally be encapsulated in microparticles. These loaded microparticles can be dispersed in aqueous vehicles containing TPGS to improve comfort. In addition, water-soluble or water-insoluble complexes of the ophthalmic agent can be incorporated in a vehicle containing TPGS. Example of water-soluble complexes include traditional complexes formed between the ophthalmic agent and caffeine, cyclodextrins, salicylates, benzoates. Examples of water insoluble complexes include ophthalmic agent - drug resin complexes.

The following examples are presented to illustrate further various aspects of the present invention, but are not intended to limit the scope of the invention in any respect.

EXAMPLE 1

The following formulations are representative of preferred compositions of the present invention.

| INGREDIENTS | FORMULATION (wt %) | | | | | | |
|---|---|---|---|---|---|---|---|
| | A | B | C | D | E | F | G |
| Sodium Diclofenac | 0.1 | 0.1 | 0.1 | 0.1 | 0.1 | — | 0.1 |
| Dexamethasone | — | — | — | — | — | 0.1 | — |
| Vitamin E TPGS (1000) | 3.0 | 3.0 | 3.0 | 3.0 | 3.0 | 3.0 | 3.0 |
| Tromethamine | 0.23 | 0.23 | 0.23 | 1.2 | 1.2 | — | 0.23 |
| Boric Acid | 1.0 | 0.1 | 0.1 | 1.5 | 1.5 | — | 1.0 |
| Mannitol | 4.0 | — | — | 3.0 | 4.0 | — | 4.0 |
| Benzalkonium Chloride | 0.01 | 0.01 | 0.01 | 0.01 | 0.01 | 0.01 | — |
| NaCl | — | 0.7 | 0.7 | — | — | — | — |
| Disodium EDTA | 0.1 | 0.1 | 0.1 | 0.1 | 0.1 | — | — |
| HPMC | — | 0.1 | 0.3 | 0.1 | 0.3 | — | — |
| Arginine | — | — | — | 0.5 | — | — | — |
| HCl and/or NaOH | pH to 7.4 | | | | | | |
| Purified Water | q.s. 100% | | | | | | |

Preparation:

Formulation D was prepared as follows, and Formulations A–C and E–G were prepared similarly.

A 10% (w/v) stock solution of vitamin E TPGS was prepared as follows. Approximately 150 g of vitamin E TPGS was melted in a beaker by heating on a hot plate with stirring to ensure homogeneity. About 100 grams (g) of the molten TPGS was then added into 800 milliliters (mL) of near-boiling double distilled water. This mixture was stirred and allowed to cool to room temperature to ensure complete dissolution. Sufficient water was then added to the above solution to make a liter of stock solution.

Sodium diclofenac (0.3 g) was added to 90 mL of 10% TPGS stock solution. After complete dissolution of the diclofenac, the each of following ingredients were sequentially added to the solution with stirring so that each ingredient was completely dissolved before the next ingredient was added: 1.5 g of arginine, 9.0 g of mannitol, 4.5 g of boric acid, 3.6 g of tromethamine and 0.3 g of edetate sodium. To the above solution was added 6.0 mL of 0.5% solution of benzalkonium chloride, followed by the addition of 15 mL of 2% solution of HPMC. An additional 150 mL of water were added and the pH of the formulation adjusted to 7.4 with HCl and/or NaOH. To the resulting solution, enough water was added to bring the total solution volume to 300 mL. The osmolality of the final solution was about 300 mOsm/kg.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for treating or controlling ocular inflammation, comprising the topical ocular application of an ophthalmic composition wherein the ophthalmic composition comprises:

a therapeutically effective amount of one or more ophthalmic agents selected from the group consisting of non-steroidal anti-inflammatory agents and steroidal anti-inflammatory agents;

an amount of a polyoxyalkylene glycol ester of a vitamin E tocopheryl ester of a dicarboxylic acid effective to reduce the discomfort and irritation associated with topical ophthalmic administration of said ophthalmic agent; and an ophthalmically acceptable aqueous vehicle, wherein the aqueous vehicle does not comprise liposomes.

2. The method of claim 1, wherein ophthalmic agent is a the non-steroidal anti-inflammatory agent comprising an aryl- or heteroaryl-alkanoic acid, or an ophthalmically acceptable salt, ester or amide thereof.

3. The method of claim 2, wherein the non-steroidal anti-inflammatory agent is selected from the group consisting of diclofenac and its ophthalmically acceptable salts, esters or amides.

4. A method for improving comfort and reducing irritation in ophthalmic compositions containing one or more ophthalmic agents which are irritating to the eye, comprising the step of adding to the ophthalmic composition an amount of a polyoxyalkylene glycol ester of a vitamin E tocopheryl ester of a dicarboxylic acid effective to reduce the discomfort and irritation associated with topical ophthalmic administration of said ophthalmic agent.

5. The method of claim 4, wherein the polyoxyalkylene glycol ester of a vitamin E tocopheryl ester of a dicarboxylic acid is selected from one or more polyoxyethylene glycol esters of a vitamin E tocopheryl ester of succinic acids wherein the polyoxyethylene glycol moiety of the ester has a molecular weight in a range between about 600 and about 6000.

6. The method of claim 5, wherein the polyoxyethylene glycol moiety of the ester has an average molecular weight of about 1000.

7. The method of claim 4, wherein the concentration of polyoxyalkylene glycol ester of a vitamin E tocopheryl ester of a dicarboxylic acid is less than about 30 percent by weight.

8. The composition of claim 7, wherein the concentration of polyoxyalkylene glycol ester of a vitamin E tocopheryl ester of a dicarboxylic acid is between about 0.1 and about 20 percent by weight.

9. The composition of claim 8, wherein the concentration of polyoxyalkylene glycol ester of a vitamin E tocopheryl ester of a dicarboxylic acid is between about 0.5 and about 10 percent by weight.

* * * * *

UNITED STATES PATENT AND TRADEMARK OFFICE
CERTIFICATE OF CORRECTION

PATENT NO. : 5,886,030
DATED : March 23, 1999
INVENTOR(S) : Maniar

It is certified that error appears in the above-identified patent and that said Letters Patent is hereby corrected as shown below:

Claim 8 should read: "The method of claim 7 ....." instead of "The composition of claim 7 ....."

Claim 9 should read: "The method of claim 8 ....." instead of "The composition of claim 8 ....."

Signed and Sealed this

Twenty-eighth Day of September, 1999

Attest:

Q. TODD DICKINSON

*Attesting Officer*  *Acting Commissioner of Patents and Trademarks*